(12) United States Patent
Meyer et al.

(10) Patent No.: US 8,216,657 B2
(45) Date of Patent: Jul. 10, 2012

(54) PREFORM FOR MAKING A PROSTHETIC LIMB SOCKET

(75) Inventors: Robert B. Meyer, Lewisburg, OH (US); Wilbur N. Meyer, Brookville, OH (US)

(73) Assignee: Bulldog Tools, Inc., Lewisburg, OH (US)

( * ) Notice: Subject to any disclaimer, the term of this patent is extended or adjusted under 35 U.S.C. 154(b) by 158 days.

(21) Appl. No.: 12/806,598

(22) Filed: Aug. 17, 2010

(65) Prior Publication Data

US 2012/0045607 A1 Feb. 23, 2012

(51) Int. Cl.
*B32B 3/06* (2006.01)
(52) U.S. Cl. ............... 428/64.1; 428/66.3; 428/66.7; 428/67; 623/901; 623/926
(58) Field of Classification Search ............ 428/64.1, 428/66.7, 67, 66.3; 623/901, 926
See application file for complete search history.

(56) References Cited

U.S. PATENT DOCUMENTS

| | | | |
|---|---|---|---|
| 5,901,060 A | 5/1999 | Schall et al. | |
| 5,980,803 A | 11/1999 | Slemker et al. | |
| 6,106,559 A | 8/2000 | Meyer | |
| 6,551,683 B2 | 4/2003 | Meyer | |

*Primary Examiner* — Brent Ohern
(74) *Attorney, Agent, or Firm* — Jacox, Meckstroth & Jenkins

(57) ABSTRACT

A preform for making a prosthetic limb socket includes an injection molded disk of thermoplastics material, and a peripheral portion of the disk is supported by a rigid metal ring. The ring and the peripheral disk portion have an interfitting connection which permits the disk and ring to be heated in an oven. The ring and softened disk are then inverted and stretched downwardly over a positive model of a residual limb while a vacuum is introduced through holes within the model to form a plastic socket which conforms to the model. The interfitting connection may be peripherally spaced studs on the ring and projecting into corresponding holes in the disk or may be an annular rib or arcuate rib sections on the ring which project into an annular recess or arcuate cavities within the disk. After the plastic cools, the ring is separated for reuse.

20 Claims, 3 Drawing Sheets

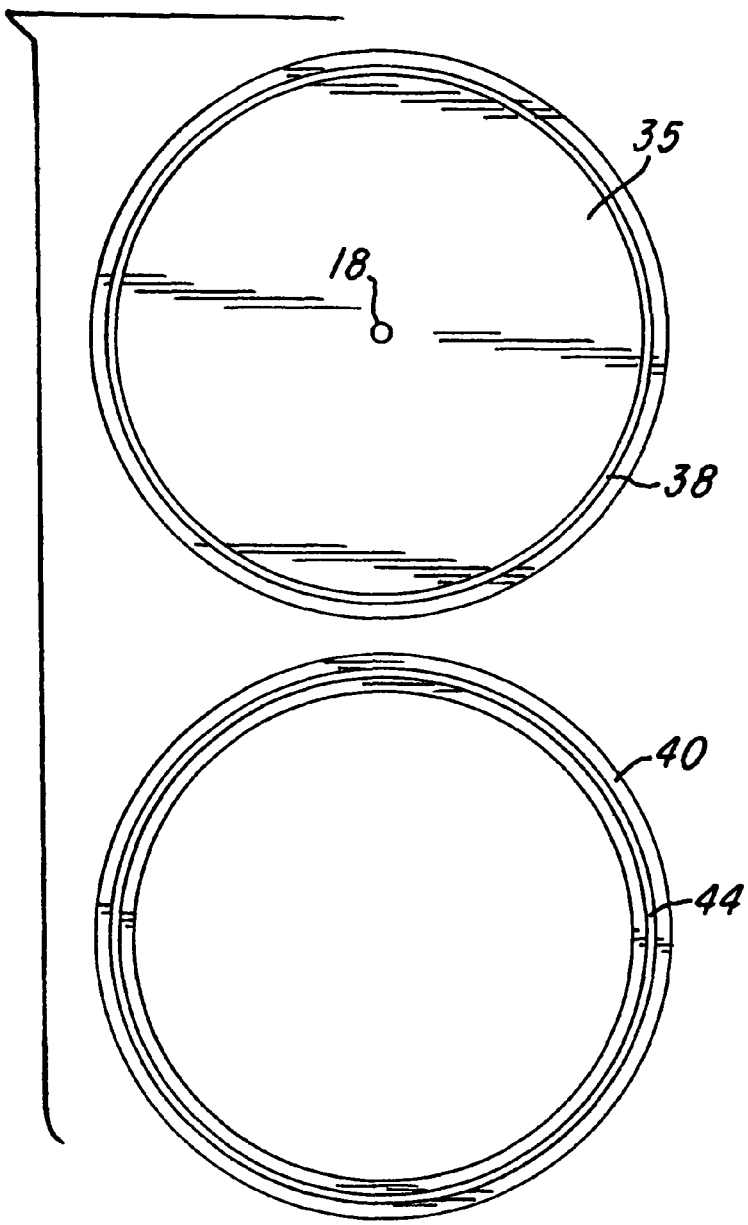
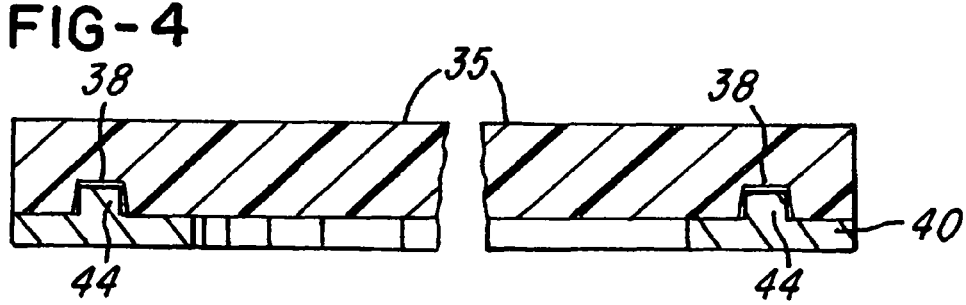

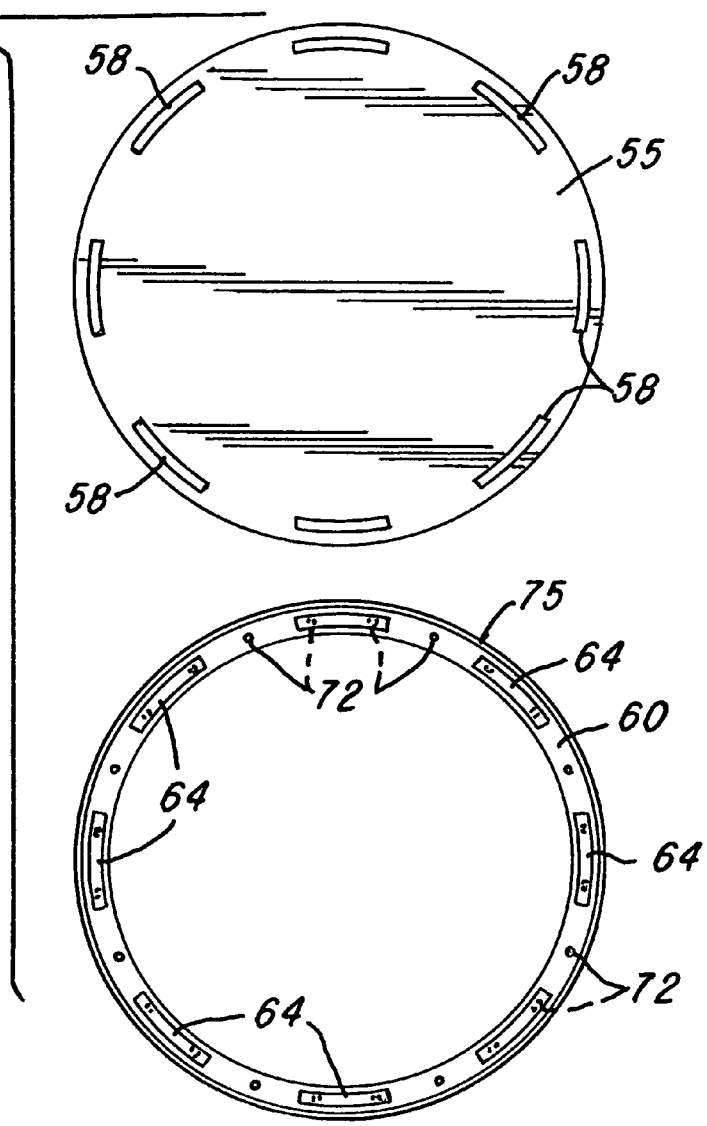
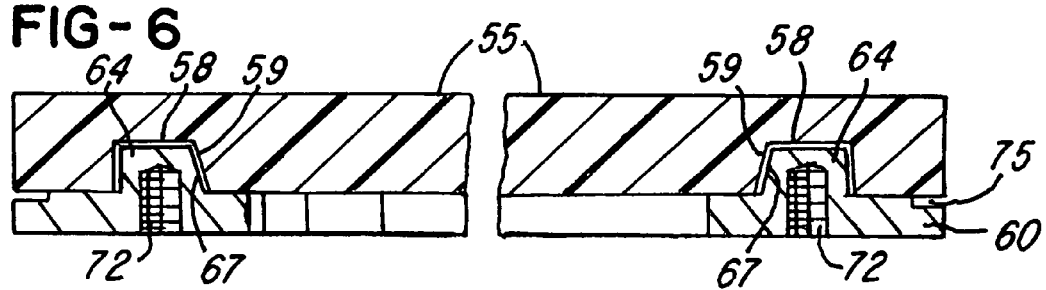

PREFORM FOR MAKING A PROSTHETIC LIMB SOCKET

BACKGROUND OF THE INVENTION

This invention relates to the production of a substantially rigid plastic socket for receiving the stump or residual limb of a partial amputee, such as, for example, a prosthetic limb socket as disclosed in U.S. Pat. No. 5,980,803 and U.S. Pat. No. 6,551,683, the disclosures of which are herein incorporated by reference. In the forming of a socket in accordance with U.S. Pat. No. 5,980,803, it is common to extrude a large rectangular flat sheet of thermoplastics material and with a predetermined thickness, such as one-half inch, and then cut the sheet into a plurality of smaller square pieces or sheets, for example, 24 inch square sheets. A peripheral portion of a square sheet is clamped within a square metal clamping frame and the square frame and sheet are placed within an oven having a temperature of about 400° F. and until the square plastic sheet softens. The heated square plastic sheet and the attached square frame are then removed from the oven by manually gripping the frame with protective gloves, and the sheet is drawn and stretched downwardly over a hollow positive model of the stump or residual limb.

In accordance with U.S. Pat. No. 6,551,683, which issued to an inventor of the present invention, a metal reinforcing ring is molded within a peripheral portion of an injection molded disk. The positive model is commonly mounted on a vacuum base or pedestal which creates a vacuum within the hollow model and through fine holes or pores within the model while the heated plastic sheet or disk is stretched over the model to form a socket conforming to the model. The positive model of the patient's residual limb is commonly produced by forming a plaster cast on the patient's residual limb, removing the cast after it hardens and filling the cast with a plaster to make a positive model. The cast is then removed or broken away from the positive model with a pneumatic chisel. A positive model may also be made, for example, as disclosed in U.S. Pat. No. 5,901,060, that is, by using a digitized impression of the residual limb to machine the model. After a socket is formed, it usually receives a coupler such as the socket coupler disclosed in U.S. Pat. No. 6,106,559 which issued to an applicant of the present invention.

It has been determined that the above method for making a socket using a square plastic sheet cut from a larger extruded sheet is slow and expensive and results in producing significant scrap from the sheet, primarily due to the square corner portions of the sheet which are scrapped along with the trimmed base portion of the drawn sheet used to form the socket. Also, the clamping frame for the rectangular sheet is relatively expensive, has a limited service life, and requires significant time to be properly attached to the peripheral portion of the square sheet and then removed from the sheet after the heated sheet is stretched over the positive model. The method of making the square sheet, the corner portions of the square sheet and the significant time required for attaching the clamping frame to the square sheet and removing the frame after forming a socket, add significantly to the cost of producing the socket. While the above method of making a socket with an injection molded disk having an embedded metal reinforcing ring significantly decreases the time required for making a socket, the reinforcing ring adds to the cost of the disk, and the ring is not reusable and becomes scrap along with the base portion of sheet or disk removed from the socket.

SUMMARY OF THE INVENTION

The present invention is directed to an improved preform for simplifying the making of a prosthetic limb socket and which significantly reduces the cost as well as the time required for making a prosthetic limb socket in addition to minimizing the equipment required for making a socket. In accordance with illustrated embodiments of the invention, a flat circular sheet or disk of thermoplastics material is injection molded in a circular mold cavity. A peripheral portion of the disk is formed or molded with one or more recesses or cavities for receiving a corresponding projection or circumferentially spaced projections of a disk support ring to form an interfitting connection between the molded disk and the support ring around the periphery of the disk to restrict lateral movement of the disk on the ring in all directions.

The preform molded plastic disk is heated on the support ring within an oven at a predetermined temperature, such as 400 degree F. After the plastics material softens and a center portion of the disk is drooping, the disk is removed from the oven on the support ring by manually gripping the support ring and an overlying peripheral portion of the disk with protective gloves. The preformed heated disk and the support ring are then inverted or flipped over as a unit and moved downwardly over a positive model of a residual limb. The softened center portion of the disk stretches around and conforms to the model while a vacuum is applied within the model through fine or small holes extending through the model to form a plastic socket conforming to the model. After the plastics material cools and becomes rigid, an annular base portion of the disk is trimmed from the socket to be discarded. After the base portion cools, it is separated from the interfitting support ring so that the ring may be reused with another injection molded disk of thermoplastics material.

Other features and advantages of the invention will be apparent from the following description, the accompanying drawings and the appended claims.

BRIEF DESCRIPTION OF THE DRAWINGS

FIG. 3 is a plan view of support ring and a plan view of a molded plastic disk constructed in accordance with another embodiment of the invention;

FIG. 4 is a fragmentary radial section of the interfitting plastic disk and support ring of FIG. 3 after being assembled;

FIG. 5 is a plan view of a support ring and a molded plastic disk constructed in accordance with another embodiment of the invention; and FIG. 6 is a fragmentary radial section of the interfitting plastic disk and support ring of FIG. 5 after being assembled.

DESCRIPTION OF THE ILLUSTRATED EMBODIMENTS

Figure 1:
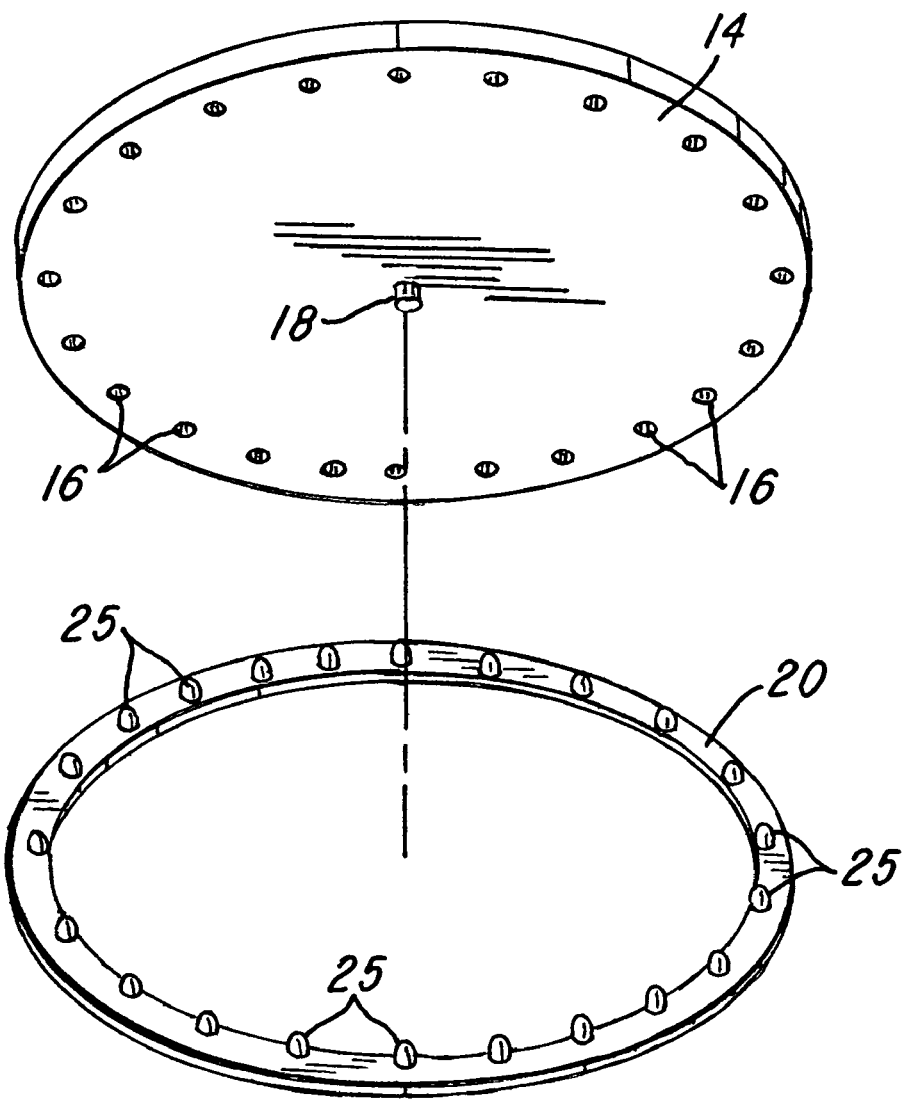
FIG. 1 is a perspective top view of a support ring and a perspective bottom view of a molded disk and showing one form of an interfitting connection between the disk and the ring in accordance with one embodiment of the invention.

FIG. 1 illustrates a preform disk 14 which is used for making a prosthetic limb socket such as disclosed in above mentioned U.S. Pat. No. 6,551,683 and which comprises a flat circular disk of a thermoplastics material such as a clear or colored polyethylene. The disk 14 has a predetermined diameter, for example, 24 inches, and has a predetermined thickness, for example, within the range of ⅜ inch to ⅝ inch, such as ½ inch. The disk 14 is injection molded within a circular mold cavity and is molded with a series of peripherally spaced cylindrical cavities 16. Preferably each circular cavity 16 is a blind cavity in that it does not extend completely through the thickness of the disk 14. The disk is also molded with a center projection 18 which is formed by the sprue bushing supported by the mold for the disk 14.

Figure 2:
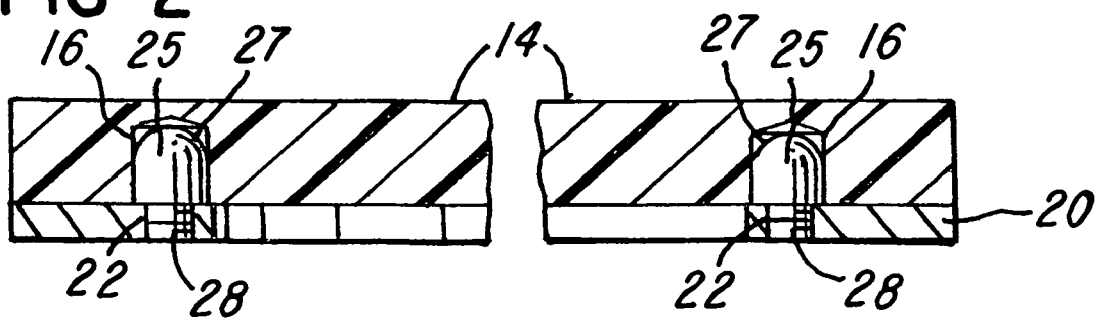
FIG. 2 is a fragmentary radial section of the interfitting ring and disk of FIG. 1 after being assembled.

The preform disk 14 receives and is supported by a flat metal support ring 20 which has a series of peripherally or circumferentially spaced threaded holes 22 each of which receives a projection 25 in the form of a stud having a rounded top surface 27 and a smaller diameter threaded base portion 28 threaded into a hole 22. As shown in FIG. 2, the studs or projections 25 extend into the cavities 16 molded within the disk 14 and form a positive interfitting connection between the plastic molded disk 14 and the metal support ring 20 around the ring and disk. The threaded holes 22 and the projections 25 are uniformly spaced around the support ring 20, and the holes or cavities 16 within the disk 14 are uniformly spaced around the peripheral portion of the disk 14 so that the disk 14 may be placed on the ring 20 without rotating or orienting the disk 14 to a particular location with respect to the ring 20. The projections 25 may also be attached by other means to the ring 20, for example, by welding, or projections may be formed as integral parts of the ring 20 by machining or casting the metal ring.

After the preformed disk 14 is inserted on the support ring 20, the assembled disk 14 and ring 20 are heated within an infrared or convection oven to a temperature to about 400 degrees F. After about 15 to 20 minutes, the plastics material softens, and a center portion of the disk 14 within the ring 20 begins to droop within the ring. The assembled heated disk 14 and support ring 20 are then inverted or flipped over and are moved as a unit downwardly over the positive model of the residual limb, as described in above-mentioned U.S. Pat. No. 6,551,683. After the center portion of the disk 14 stretches and conforms to the positive model to form a socket with the aid of vacuum being applied through fine holes within the positive model, the socket and ring 20 are allowed to cool. An annular base portion of the socket is then trimmed from the socket, and the metal ring 20 is separated from the annular base portion so that the support ring 20 may be used again with another molded plastic preform disk 14.

Another embodiment of the invention is illustrated in FIGS. 3 & 4. In this embodiment, a flat preform disk 35 is injection molded of a thermoplastics material and molded with an annular groove or recess 38 within a flat surface of the disk. A metal support ring 40 is formed with an annular rib or projection 44 which preferably is formed as an integral part of the support ring 40, but may be an attached annular projection. As shown in FIG. 4, when the preform disk 35 is placed on the metal support ring 40, the annular rib or projection 44 extends into the annular groove 38 to form a releasable interfitting positive connection between the disk 35 and ring 40. Preferably, the groove or recess 38 has slightly inclined or tapered side surfaces to facilitate convenient removal of an annular portion of the disk 35 from the ring 40 after forming of the prosthetic limb socket and the annular portion of the disk is cut from the socket.

Referring to FIGS. 5 & 6 which show another modification or embodiment of the invention, a circular plastic preform disk 55 is molded of a thermoplastics material and has a peripheral portion with a plurality of circumferentially spaced arcuate grooves or recesses 58 which are uniformly spaced and project partially into the disk 55, as shown in FIG. 6. Each of the arcuate recesses 58 has a tapered or slightly inclined inner surface 59 and may have slightly tapered opposite end surfaces. A metal support ring 60 is formed with a corresponding plurality of uniformly spaced arcuate ribs or projections 64 which are preferably formed as an integral part of the ring 60, as shown in FIG. 6. Each of the arcuate projections 64 has a slightly tapered or inclined inner surface 67, and a series of threaded holes 72 are formed within the support ring 60, with two of the holes 72 extending as blind holes within each of the arcuate ribs or projections 64. The threaded holes 72 between the arcuate projections 64 extend through the support ring 60. When the preform disk 55 is placed on the support ring 60 (FIG. 6), the arcuate ribs or projections 64 extend into the arcuate recesses or cavities 58 within the preform disk 55 to form a positive interconnection of the support ring with the preform disk.

The method of using the assembled preform disk 35 and support ring 40 (FIGS. 3 & 4) and the preform disk 55 and support ring 60 (FIGS. 5 & 6) is the same as described above in connection with the preform disk 14 and the support ring 20 (FIGS. 1 & 2). After the prosthetic limb socket is formed, and the annular base portion of the preform is cut or removed from the socket, the support ring 20 or 40 or 60 is separated and removed from the annular base portion of the socket. To facilitate the separation, an annular recess 75 (FIG. 6) may be formed within the peripheral portion of the support ring 60 to form a gap with a peripheral portion of the preformed disk 55 for inserting a sharp tool, such as a screwdriver, in order to release the annular base portion of the disk from the support ring. The uniformly spaced threaded holes 72 formed within the support ring 60, as shown in FIGS. 5 & 6, may be used for receiving a series of peripherally spaced threaded studs or projections 25, as shown in FIGS. 1 & 2, in the event a molded preformed disk 14 is preferred to have circumferentially spaced holes 16 in place of arcuate recesses 58 or an annular recess 44 to form the interfitting connection.

From the drawings and the above description, it is apparent that a plastic preform for making a prosthetic limb socket and its support ring provide desirable features and advantages. For example, by molding or forming a rigid disk of thermoplastics material and forming its metal support ring with an interfitting connection between the support ring and a peripheral portion of the disk, provides for making a prosthetic limb socket more efficiently and at a reduced cost. For example, by forming an annular recess or a series of circumferentially spaced recesses within a peripheral portion of the disk or within the ring and by forming an annular projection or a series of projections on the ring or on the disk, a disk may be simply placed on the support ring and then placed within an oven for heating.

The interfitting connection between the support ring and the plastic disk prevents a heated disk from shifting laterally relative to its support ring while the heated disk is drawn and stretched downwardly over the positive model of a residual limb by pressing downwardly on the support ring while on top of the preform disk. After the socket has been formed and trimmed to produce an annular base portion, the support ring may be quickly separated from the annular base portion of the disk, and the support ring may be reused over and over again with new preform disks. The simple and quick attachment of a disk to a support ring and the reuse of the support ring significantly reduces the time and cost for making a prosthetic limb socket.

While the forms of plastic disk and ring assembly herein described constitute preferred embodiments of the invention, it is to be understood that the invention is not limited to these precise forms, and that changes made therein without departing from the scope and spirit of the invention as defined in the appended claims.

What is claimed is:

1. A preform for making a prosthetic limb socket from a positive model of a residual limb, comprising
a disk of thermoplastics material,
a rigid reinforcing ring supporting a peripheral portion of said disk and having a melting temperature above the melting temperature of said thermoplastics material,
said ring and said peripheral portion of said disk having an interfitting connection restricting lateral movement of said disk on said ring,
said ring having a width substantially larger than the width of said positive model for drawing and stretching said disk downwardly over said model after said disk has been heated on said ring to a softening temperature, and
said interfitting connection providing for separating said peripheral portion of said disk from said ring after drawing and stretching said disk to facilitate reusing said ring.

2. A preform as defined in claim 1 wherein said interfitting connection comprises a plurality of peripherally spaced cavities within one of said disk or said ring and a corresponding plurality of peripherally spaced projections in the other of said ring or said disk extending into said cavities.

3. A preform as defined in claim 2 wherein each of said cavities and each of said projections are arcuate in configuration.

4. A preform as defined in claim 2 wherein each of said cavities and each of said projections is circular in cross-sectional configuration.

5. A preform as defined in claim 2 wherein said projections are on said ring and are integral with said ring.

6. A preform as defined in claim 1 wherein said interfitting connection comprises an annular cavity within one of said disk or said ring, and the other of said ring or said disk includes an annular projection extending into said cavity.

7. A preform as defined in claim 1 wherein said interfitting connection comprises at least one cavity within one of said disk or said ring, and the other of said disk or said ring includes at least one projection extending into said cavity.

8. A preform as defined in claim 7 wherein said cavity extends only partially into said disk, and said projection extends only into said cavity.

9. A preform as defined in claim 1 wherein said ring has peripherally spaced threaded holes extending axially into said ring, and said holes receive threaded studs of peripherally spaced projections on said ring to form said interfitting connection.

10. A preform as defined in claim 1 wherein said interfitting connection comprises peripherally spaced projections on a circular said ring and circumferentially spaced cavities within a circular said disk.

11. A preform as defined in claim 1 wherein said peripheral portion of said disk and said ring define a peripheral gap therebetween to facilitate release of said disk from said ring.

12. A preform for making a prosthetic limb socket from a positive model of a residual limb, comprising
an injection molded disk of thermoplastics material,
a rigid metal reinforcing ring supporting a peripheral portion of said disk and having a melting temperature above the melting temperature of said thermoplastics material,
said ring and said peripheral portion of said disk having an interfitting connection restricting lateral movement of said disk in any lateral direction on said ring,
said ring having a width substantially larger than the width of said positive model for drawing and stretching said disk downwardly over said model after said disk has been heated on said ring to a softening temperature, and
said peripheral portion of said disk being separable from said ring after drawing and stretching said disk to facilitate reusing said ring.

13. A preform as defined in claim 12 wherein said interfitting connection comprises a plurality of peripherally spaced cavities molded within said peripheral portion of said disk, and said ring has a corresponding plurality of peripherally spaced projections extending into said cavities.

14. A preform as defined in claim 13 wherein each of said cavities within said disk and each of said projections on said ring are arcuate in configuration.

15. A preform as defined in claim 13 wherein each of said cavities within said disk and each of said projections on said ring is circular in cross-sectional configuration.

16. A preform as defined in claim 13 wherein said projections on said ring are integral with said ring.

17. A preform as defined in claim 12 wherein said interfitting connection comprises an annular cavity within said peripheral portion of said disk, and said ring includes an annular projection extending into said cavity.

18. A preform as defined in claim 12 wherein said interfitting connection comprises at least one cavity within one of said disk or said ring, the other of said disk or said ring includes at least one projection extending into said cavity, said cavity extends only partially into said disk or said ring, and said projection extends only into said cavity.

19. A preform as defined in claim 12 wherein said interfitting connection comprises peripherally spaced projections on one of said ring or said disk and circumferentially spaced cavities within the other of said ring or said disk.

20. A preform as defined in claim 12 wherein said peripheral portion of said disk and said ring define a peripheral gap therebetween to facilitate release of said disk from said ring.

* * * * *